United States Patent [19]
Conte et al.

[11] Patent Number: 6,155,259
[45] Date of Patent: Dec. 5, 2000

[54] BARRIER DEVICE FOR CONTRACEPTION AND PREVENTION OF SEXUALLY TRANSMITTED DISEASES

[75] Inventors: Maurice S. Conte; Julio C. Medina, both of Houston; Albert J. Scheckelhoff, Humble, all of Tex.

[73] Assignee: Total Arts Syndicators, Inc., Houston, Tex.

[21] Appl. No.: 09/228,709

[22] Filed: Jan. 12, 1999

[51] Int. Cl.[7] ........................................................ A61F 6/06
[52] U.S. Cl. ............................................. 128/830; 128/833
[58] Field of Search ................................... 128/830, 831, 128/832, 833, 839; 604/55, 286

[56] References Cited

U.S. PATENT DOCUMENTS

| | | | |
|---|---|---|---|
| 4,186,742 | 2/1980 | Donald | 128/270 |
| 4,309,997 | 1/1982 | Donald | 128/270 |
| 4,393,871 | 7/1983 | Vorhauer et al. | 609/58 |
| 4,693,705 | 9/1987 | Gero | 604/55 |
| 4,832,052 | 5/1989 | Mohajer | 128/839 |
| 4,922,928 | 5/1990 | Burnhill | 128/832 |
| 5,417,224 | 5/1995 | Petrus et al. | 128/833 |

*Primary Examiner*—Michael A. Brown
*Attorney, Agent, or Firm*—Howrey Simon Arnold & White, LLP

[57] ABSTRACT

An improved sponge device is presented having one loop-chord placed entirely within or through the sponge device to facilitate insertion and removal of an attached ovoid sponge device into and from a body cavity. The improved sponge device can be cylindrical or egg-shaped like design,—which shall be utilized depending upon manufacturing capabilities available. The improved sponge device can be impregnated with; specific spermicides, anti-infectives, lubricants, hormones, antioxidants, amino acids, and other appropriate medicaments, to allow release of impregnated solution(s) from the device into the body cavity. Closely controlled impregnation and/or coating of the sponge device is achieved by a method of manufacture employing one or more methods for impregnating and one or more methods for possible lubrication.

20 Claims, 5 Drawing Sheets

BARRIER DEVICE FOR CONTRACEPTION AND PREVENTION OF SEXUALLY TRANSMITTED DISEASES

BACKGROUND OF THE INVENTION

1. Field of the Invention

This invention relates to a sponge device and more particularly to an ovoid, cylindrical or egg-shaped like barrier device configured for ease of insertion, anatomical fit, and removal, and having predetermined quantities of spermicides, hormones, anti-virals, anti-oxidants, anti-fungals, anti-infectives, anti-neoplastic agents, steroids, surfactants and lubricants placed within the device.

2. Background of the Invention

It is well known that in recent years there has been a steady increase in the number of sexually transmitted diseases (STD) and unwanted pregnancies throughout the world. In an effort to stem the rise of these unwanted pregnancies, many types of contraceptive devices are being utilized. Oral contraceptives and intrauterine devices (IUD) are two very popular contraceptive methods. However, not all women are capable of using oral contraceptives, and IUDs produce numerous documented side effects. Other types of contraceptives, including barrier contraceptives, have gained in popularity due to the rise of STDs. Popular barrier contraceptives include condoms, diaphragms, sponges, cervical caps, spermicidal creams, foams, foaming tablets, films and melting suppositories. The diaphragm or cervical cap must be fitted by trained medical personnel, whereas condoms may require the participation of the partner. Foams, jellies, tablets and suppositories are often messy to use, and frequently cause irritation to the user and/or partner.

Developments in contraceptive methods allow a barrier, such as a sponge or sponge device, to be impregnated with a spermicide and various other agents. The impregnated barrier not only physically prevents the passage of sperm or STDs but also chemically destroys (kills) the sperm or infective agents associated with many STDs. This represents a spermicidal impediment by physical contact, which allows a single impregnated sponge device to continue to destroy sperm throughout repeated sexual encounters—up to twenty-four (24) hour period of time.

Prior art as provided to the movant, has employed as described in U.S. Pat. No. 4,393,871, gradual release of spermicide from a sponge device can be achieved by placing the spermicide into the pre-polymer material during the polymerization of the sponge device. The spermicide/surfactant is thereby molded to form the polyurethane sponge device. In order to activate the sponge device of U.S. Pat. No. 4,393,871, tap water must be added at the site. Too large an amount of water can unduly dilute the spermicide (s), possibly rendering it ineffective. Further, tap water at the site may he contaminated, or may contain chlorine which could possibly interfere with the spermicide or cause infection.

Conversely, too small an amount of water can cause a strong presence of the spermicide leading to irritation and/or allergic reaction as described in U.S. Pat. No. 4,693,705. As outlined in U.S. Pat. No. 4,693,705, recent advances suggest a more controlled concentration of spermicide. Accordingly, it is advantageous that the spermicide be placed already in solution within the sponge and at controlled concentration such that the spermicide is active and ready to use at the site. Mixing with tap water is therefore not required.

Impregnating a sponge with a solution such that it is ready to use at the site presents many advantages over the patents described above. However, the soaked sponge device must maintain its shape as a physical barrier while packaged and during insertion. Further, it must also withstand shear forces during placement and subsequent removal. Current sponges which use a single string placed through only a portion of the sponge material can pull through the sponge upon removal. Examples of sponges which use only a small portion of their geometry for receiving a string or tied loop are described in U.S. Pat. Nos. 4,186,742; 4,309,997; and 4,693,705. Another exemplary attachment scheme showing a loop affixed to the outside surface of the sponge is demonstrated in U.S. Pat. No. 4,393,871. A slight pull upon the string or loop can cause a single string shown in U.S. Pat. Nos. 4,186,742 and 4,309,997 to pull through the body, can cause a loop shown in U.S. Pat. No. 4,393,871 to pull from the body's outer surface, or a knot and surrounding small portion of the body shown in U.S. Pat. No. 4,693,705 to dislodge from the body. It is necessary to note, that a future source of infection may arise if any portion of the sponge material is allowed to remain in the body cavity for an extended period of time. Moreover, "Toxic shock syndrome", may arise in instances where an infective site is allowed to remain within a body cavity, such as the vaginal canal, for an extended period of time.

A properly inserted and removed sponge or device, not only enhances the benefits of the device, but also maintains long-term effect while positioned. Ease of positioning or insertion is equally important as maintaining the sponge's integrity during removal. A sponge, having a doughnut or flattened shape as shown in U.S. Pat. No. 4,393,871 may easily fold thereby failing to present equal radial pressure against the cavity wall. A passage may therefore be formed in those areas devoid of pressure as a result of the fold.

As defined herein, "spermicide" is a chemical placed in solution, and which provides a chemical barrier against sperm and organisms responsible for STDs. Therefore, "spermicides" used herein include an anti-infective agent.

Spermicides have, in many instances, been found to be active against herpes, gonorrhea, syphilis, trichoinonas, candida, and even HIV. Popular spermicides include benzalkonium chloride, chlorhexidine, gluconate, menfegol, octoxynol and nonoxynol-9. Nonoxynol-9 is a spermicide which acts by destroying the cell wall of the sperm, and is believed to act in the same manner on bacteria and viruses.

As defined herein, "sponge device" refers to any porous device which can be inserted into a physiological cavity. The sponge device includes any porous substance which is capable of being impregnated and/or coated. The sponge device is capable of being placed to a body cavity of a human female. The sponge device can be used to coat the cavity with hormones, amino acids, anti oxidants, lubricants, etc. Further, the sponge device can receive solutions which will reduce or prevent unwanted pregnancies, transfer of disease, growth of a virus fungus, etc. Certainly, the term "device" would include a sponge normally used for insertion into the vaginal canal of a human female.

SUMMARY OF THE INVENTION

The problems outlined above are in large part solved by the improved sponge device of the present invention. An optimal shape appears to be an ovoid ball having radially expandable pressure against all sides of the cavity wall, since the ovoid ball will be compressed to an outer dimension less than the original expanded dimension during placement. The result will be the lubrication and coating of vaginal mucosa with the appropriate medicament.

That is, the device hereof is either ovoid, cylindrical, or egg-shaped like in design and substantially resistant to severe folding or deformation during placement. The sponge device can be easily inserted and completely removed by utilizing a chord placed partially or entirely through the elliptical sponge device. The chord is shaped as a loop and presents ease of insertion by extending pressure between the ovoid and the loop such that the ovoid can be accurately and precisely placed in a compressed or deformed state, whereby the compression coats the surrounding wall by exudation of medicaments. Once placed, the device expands and thereafter exists as a complete physical barrier within the cavity. After placement, the sponge device is radially conformable against the walls of a body cavity or vaginal canal of fluctuating inner diameter. Thus, the sponge device is capable of retaining equal radial pressure against the body cavity wall. As with insertion, the loop is used to facilitate extraction as well, by simple reversal of insertion process, or another more anatomical procedure or method would be by performance of the "Kegle" maneuver, (i.e. the contracting and relaxing of the pelvic floor muscles which control the flow of urine and therefore can facilitate expulsion of the ovoid ball.) Moreover, the sponge is pre-packaged and shipped ready to use with a properly controlled solution of spermicide, anti-infectives, anti-fungals, anti-virals, hormones, amino acids and/or antioxidants impregnated as a solution therein.

In simpler terms, the present invention contemplates an improved sponge device comprising of a porous ovoid design, having a homogeneous porosity, and a partial passage placed through the center of the sponge device, to depth of 65% (±1%) of the ovoid diameter. A chord is placed through the opening for attachment to the ovoid sponge device for extraction by an anchor or other means. If desired or needed, a lubricant may be added to the surface of the sponge device after the loop-anchor attachment.

BRIEF DESCRIPTION OF THE DRAWINGS

Other objects and advantages of the invention will become apparent upon reading the following detailed description and upon reference to accompanying drawings in which.

Figure 1:
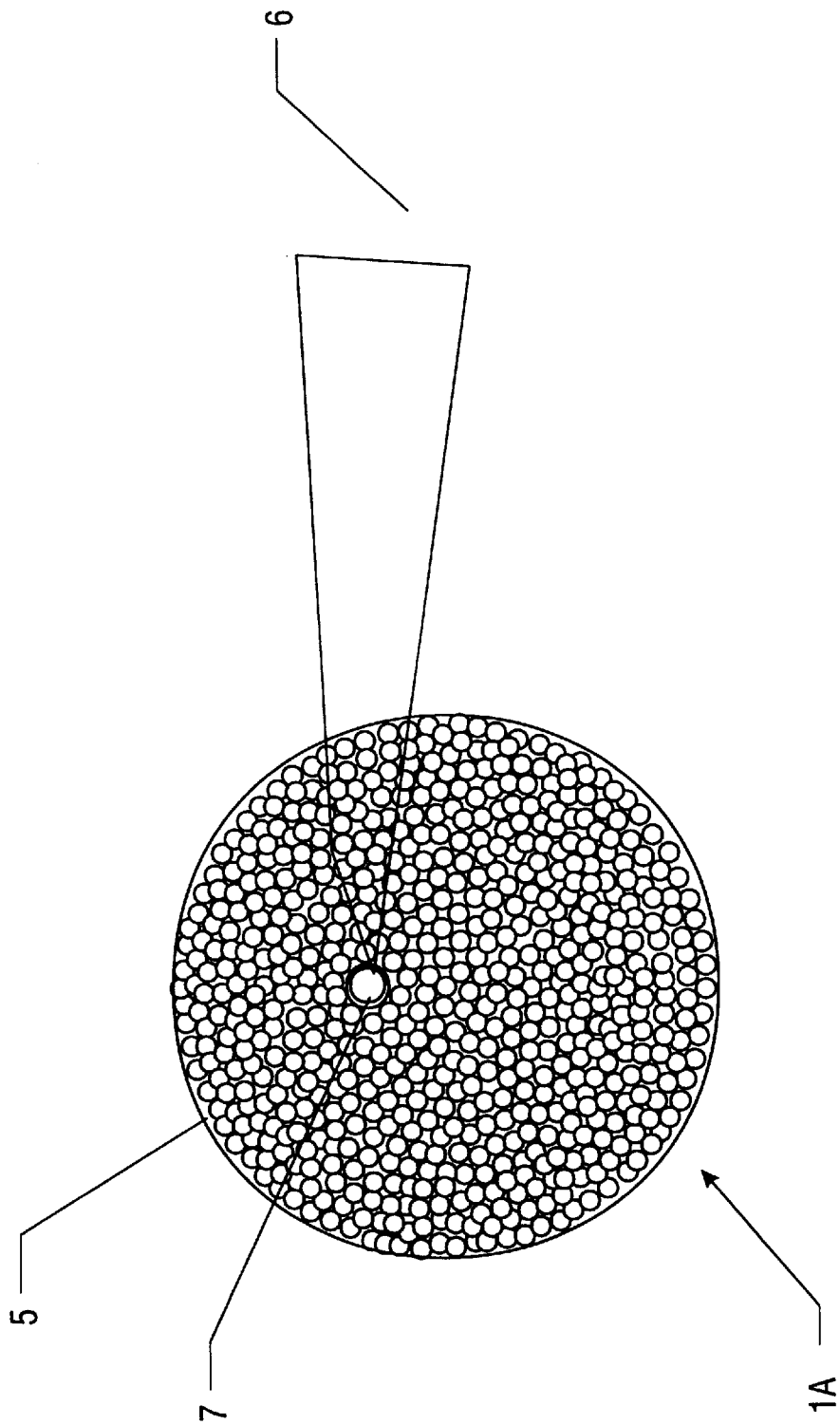
FIG. 1 is a cross-sectional view of a sponge device along the short axis according to the present invention.

While the invention is susceptible to various modifications and alternative forms, specific embodiments thereof are shown by way of example in the drawings and will herein be described in detail. It should be understood, however, that the drawings and description thereto are not intended to limit the invention to the particular forms disclosed, but on the contrary, the intention is to cover all modifications, equivalents and alternatives falling within the spirit and scope of the present invention as defined by the appended claims.

DESCRIPTION OF ILLUSTRATIVE EMBODIMENTS

Turning now to the drawings, FIG. 1 illustrates a sponge device 1A according to the present invention. Sponge device 1A includes a ovoid design 5 having a polymeric sponge-like structure. Ovoid design 5 can be of any size sufficient to be slightly compressed (i.e., radially compressed inward from its uncompressed size, so as to fit snugly within the body cavity after compression is released). Ovoid design 5 can be easily inserted into the cavity without the need for orientation. Further, there is no need for a special applicator. The material of ovoid design 5 is preferably a soft, lightweight, physiologically inert polymeric foam of polyurethane, polyether, polyester, or the like, which is of an appropriate porosity and which, when released from compression, will return to substantially its original shape. Such foam materials are known to those skilled in the art. The sponge device is preferably derived from a type of foam which results in a smooth, continuous porous outer and inner surface. As an example, the ovoid design 5 can be cut approximately 40 mm in diameter by 60 mm in length for placement in a vaginal canal of a human female, to cover the cervical area, while permitting intercourse to occur. A variance of thirty-five to fifty millimeter appears to be the optimal range in diameter for such an exemplary purpose. Additionally, the term "ovoid" or shape shall be implicitly understood to also include; cylindrical or egg-shaped like design—which shall be utilized depending upon manufacturing capabilities.

Placed partially through ovoid design 5 is a passage 7 (see FIG. 2) having a predetermined diameter (e.g., 1.0 to 1.5 mm). Such passage can also be referred to as an opening. A chord with anchor is configured to extend, for insertion through, into passage 7. The chord with anchor will be comprised of chord formed into a loop, attached to a disc or "button" configuration to serve as flanged anchor to retain chord within the sponge device for insertion and extraction from the body cavity. When placed inside the passage, the foam interior yields to the flanged anchor, securing the anchor inside the passage. Chord 6 is composed of cotton, polyester, or any physiologically inert material which is soft yet sturdy enough to withstand stress after long periods of immersion within a solution. Chord 6 can be approximately 1.0 mm to 2.0 mm in diameter and several hundred millimeters long depending upon the diameter of device 5. Chord 6 can either have a circular diameter or can be rectangular in cross-section as shown in FIG. 1. Furthermore, when grasped and pulled, using chord 6, this compresses the ovoid design 5 where it can be more easily inserted and removed.

Figure 2:
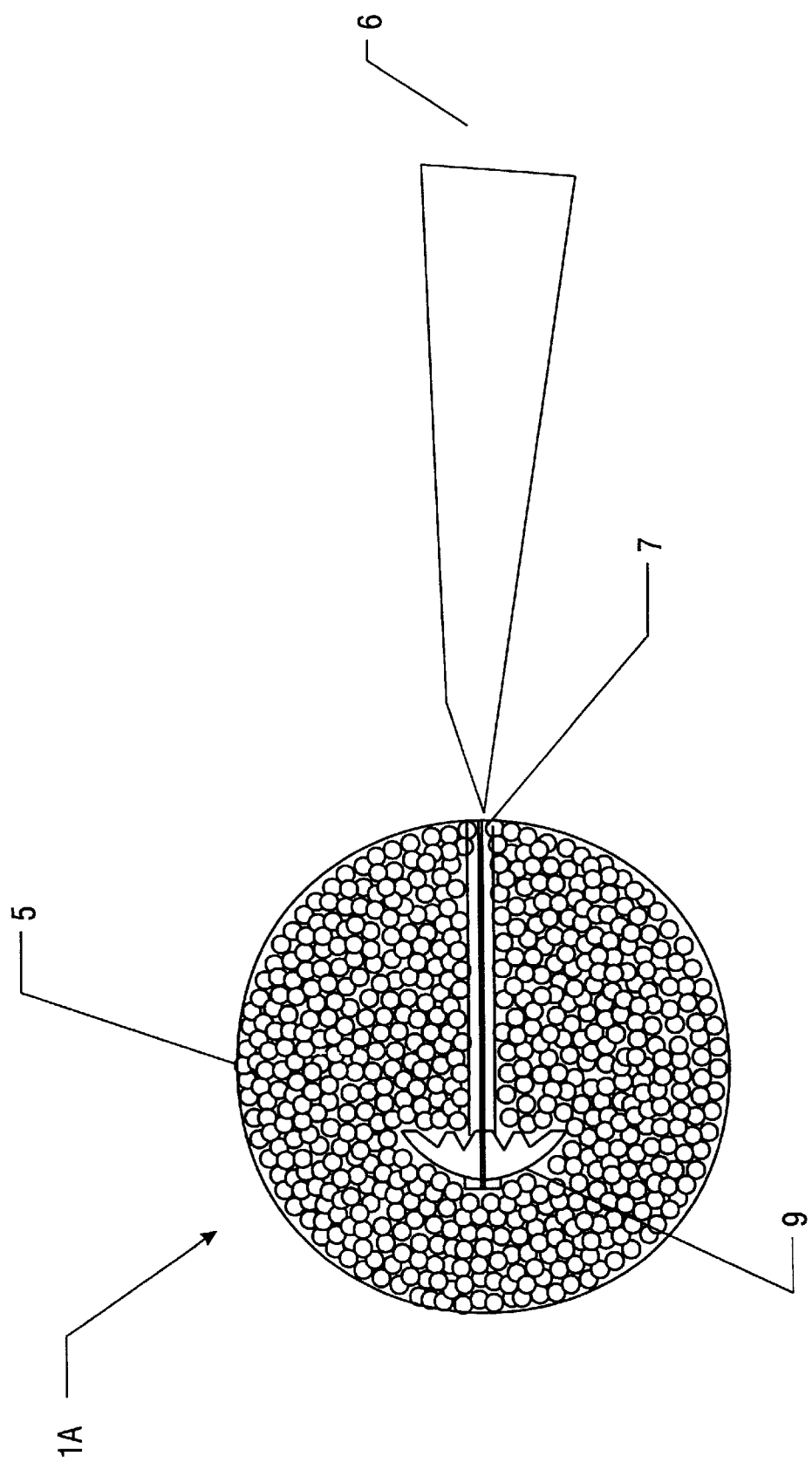
FIG. 2 is a cross-sectional view of a sponge device along the long axis according to the present invention.

Referring to FIG. 2, a cross-sectional view of ovoid design 5, passage 7 and chord 6 are shown. Chord 6, being flexible and resilient to tear, attaches a disk or button to cross-sectional diameter depth of passage 7 in a predetermined percentage (e.g., at least 65% but no more than 70%) of the total cross-sectional diameter depth of ovoid design 5. By placing passage 7 through a diameter depth area through the center of ovoid design 5, sufficient cross-sectional depth is attached and anchored to ensure depth of passage 7 is equidistant from the opening's lateral sides.

Spermicides known to medical science may be used. Potential spermicide candidates include nonoxynol-9 sodium oxychlorosene, alkylphenoxy polyethoxy ethanol, benzalkonium chloride, etc. The sponge device may also be impregnated with anti-infective agents including antibiotics such as bacitracin, neomycin, polymyxin B, penicillin, tetracycline, chloramphenicol, erythromycin, sulfonamid, nitrofurazone, and providone-iodine. Iodine may be dissolved in a surfactant such as nonoxynol-9 and impregnated into the sponge device. Chlorhexidine gluconate may serve the same purpose. Other medications such as anti-inflammatory compounds including steroids, antifungal agents including miconazole, and anti-viral drugs including acyclovir or interferon may be incorporated in the sponge device, depending upon the desired therapeutic or prophylactic effect, and the time span for which the device provides therapy.

Furthermore, amino acids, hormones, and antioxidants may be placed within the sponge device. Lubrication for vaginal dryness includes glycerin and sorbic acid. Hormonal preparations for atrophic vaginitis may include estrogen and progesterone compounds. Amino acids may be added to treat cervicitis and cervical lesions by facilitating wound healing and epithelization. Antioxidants may include vitamin A or vitamin E to impede development of leukoplakia, a pre-cancerous lesion. Preservatives and pH adjusters may also be added. An acid environment decreases sperm mobility and inactivates gonococcus. A deodorant, such as pectin, may also be added to the sponge device for aromatic purposes. A fragrance may also be added, as well as a flavoring agent.

Figure 3B:
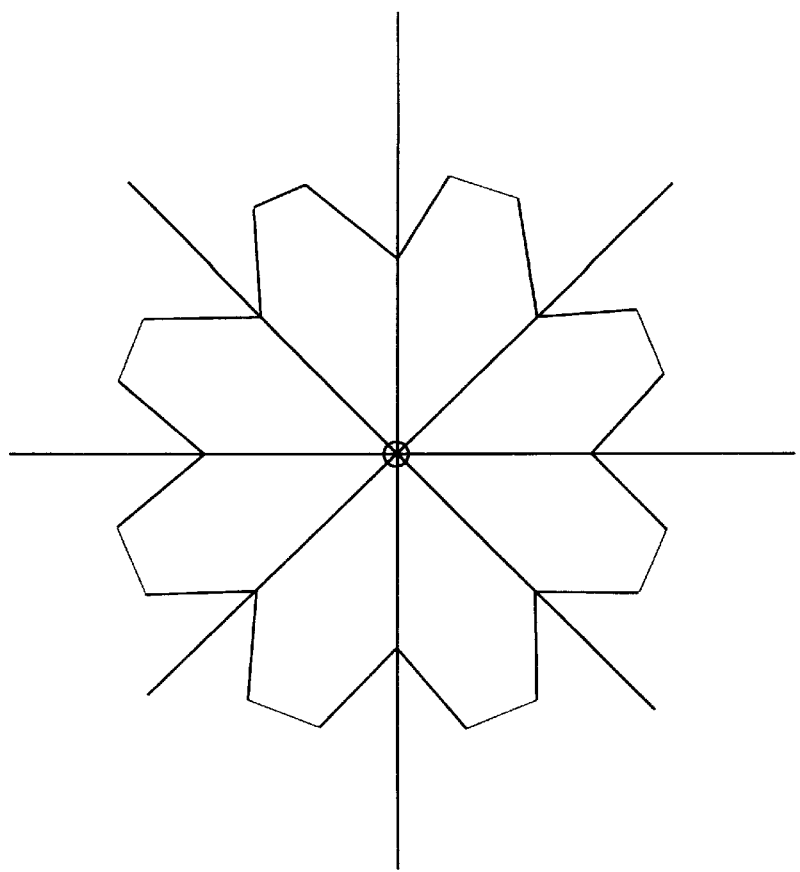
FIG. 3 is a view of a loop-anchor attachment of a sponge device according to the present invention.
Figure 3A:
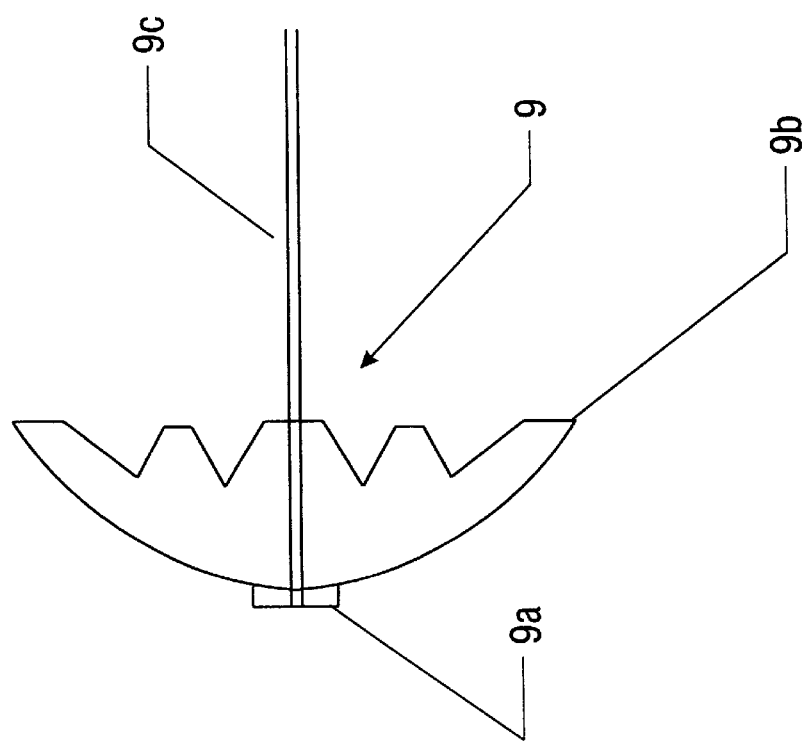

Referring to FIG. 3, the disk anchoring device is affixed to the chord by means of a copper, or other suitable metal brad attachment, or suitable adhesive method. Such anchoring device can also be referred to as a button, umbrella or bottle-cap.

Figure 4:
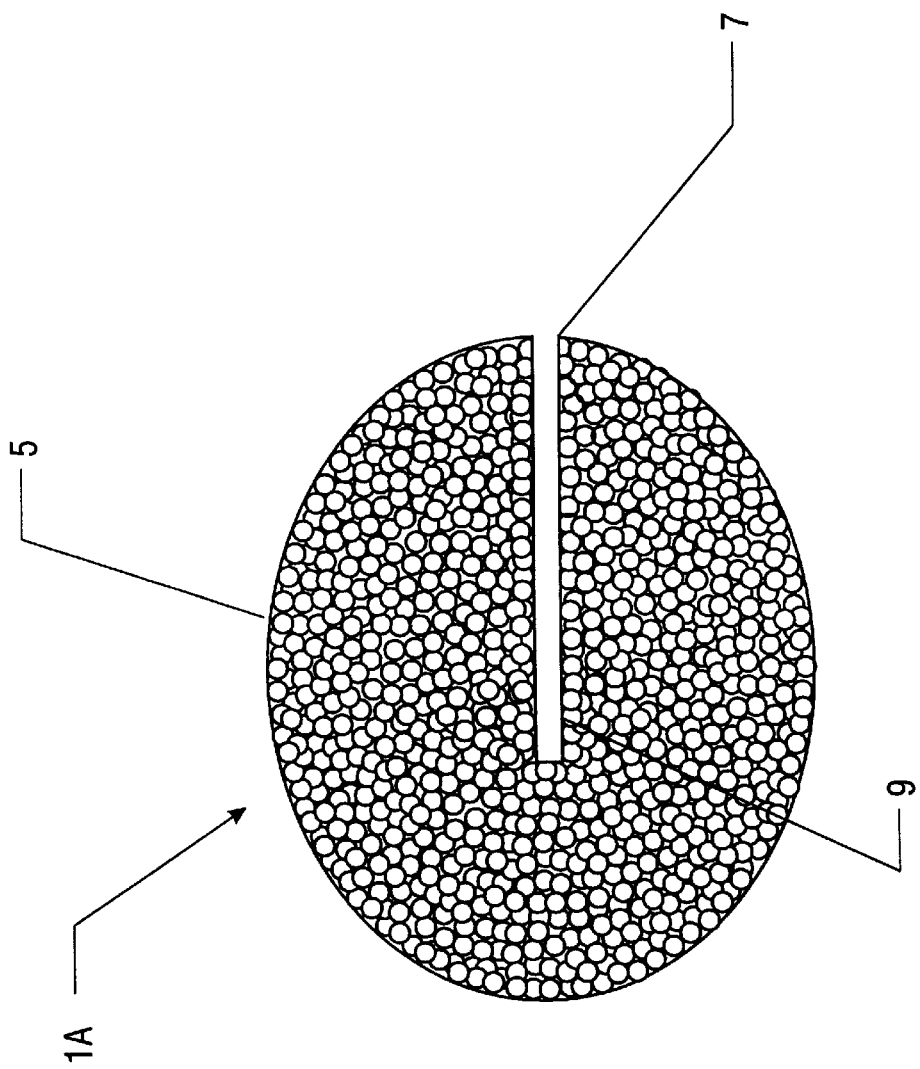
FIG. 4 is a cross sectional view of a sponge device, showing placement of a channel for insertion of a loop-anchor attachment.

Referring to FIG. 4, a channel with a diameter of between 1 and 1.5 millimeters is placed into the center of the sponge device 5, with a depth of approximately 65% of the diameter.

Figure 5A:
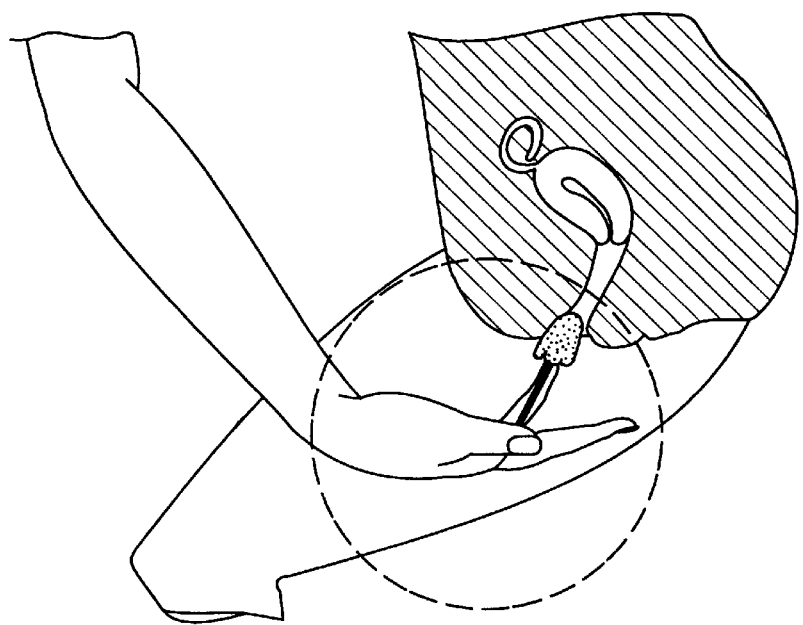
FIG. 5a is a detail view of FIG. 5.
Figure 5B:
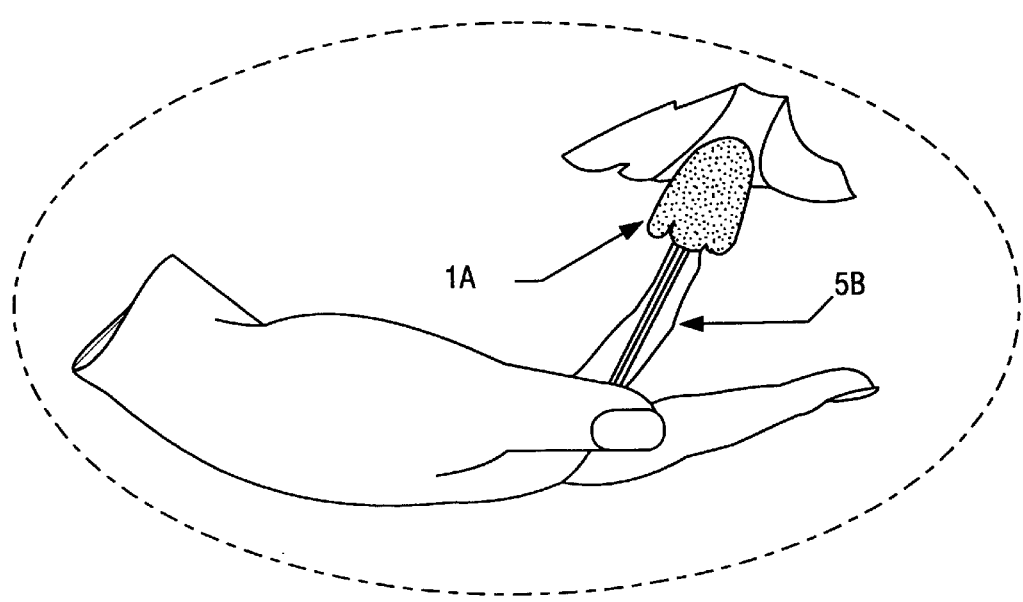
FIG. 5 is a sponge device shown in a compressed state for insertion into a body cavity according to the present invention.

Referring to FIG. 5, sponge device 1A is shown appropriately grasped for placement into a body cavity. The compressed geometry can therefore be placed into a body cavity of lesser diameter than the uncompressed ovoid thereby allowing the compressed geometry to radially expand equally against the entire surrounding cavity wall.

Referring to FIG. 5, sponge device 1A is easily inserted into the cavity area using an extended forefinger 5b placed between device 5 and the inner surface of one or more chords 6. Sponge device is inserted before sexual intercourse and should remain within the cavity for at least two to six hours after intercourse. During insertion, moisturizer/lubricant agents within the outer region also coat the cavity wall. Throughout the recommended wearing period, spermicide/anti-infectives are released from device 5 and into the cavity area. Sponge device 1A is removed by grasping the flexible chord with the fingers and pulling the attached device 5 from cavity 5a. Chord 6 may be adhesively bonded to one or more areas within its respective passage 7. However, it is not necessary that it be bonded, and in some instances, chord 6 should remain freely moving through it's respective passages. Certainly, sponge devices employing non-bonded cords would be easier to manufacture than if the cords are bonded.

It will be appreciated to those skilled in the art having the benefit of this disclosure that this invention is believed to be capable of insertion into numerous body cavities of various sizes and shapes. Furthermore, it is also to be understood that the form of the invention shown and described is to be taken as presently preferred embodiments. Various modifications and changes may be made without departing from the spirit and scope of the invention as set forth in the claims. An exemplary modification might be one which uses only one passage and chord, or more than two passages and two chords, while employing an ovoid, cylindrical, or egg-shaped like sponge design. It is intended that the following claims be interpreted to embrace all such modifications and changes.

What is claimed is:

1. A sponge device, comprising:
   a porous ovoid device having a long axis and short axis;
   a passage of a predetermined diameter located along the long axis of the ovoid device and placed to a predetermined depth within said ovoid device;
   a chord extending into said passage and fixedly attached to the ovoid device by an attachment means, said attachment means located within said passage;
   a medicament solution placed within the pores throughout the ovoid device; and
   a lubricant applied to the surface of said device.

2. The sponge device as recited in claim 1, wherein said attachment means is an anchor configuration.

3. The sponge device as recited in claim 1, wherein said attachment means is a button configuration.

4. The sponge device as recited in claim 1, wherein said attachment means is an umbrella configuration.

5. The sponge device as recited in claim 1, wherein said attachment means is a bottlecap configuration.

6. The sponge device as recited in claim 1, wherein the ratio of the long axis to the short axis is 3 to 2.

7. The sponge device as recited in claim 1, wherein the predetermined depth of the passage is over 50% of the length of the long axis.

8. The sponge device as recited in claim 1, wherein the predetermined depth is 65% of the length of the long axis.

9. The sponge device as recited in claim 1, wherein said attachment means is an anchor configuration.

10. The sponge device as recited in claim 1, wherein said attachment means is a button configuration.

11. The sponge device as recited in claim 1, wherein said attachment means is an umbrella configuration.

12. The sponge device as recited in claim 1, wherein said attachment means is a bottlecap configuration.

13. The sponge device as recited in claim 1, wherein the ratio of the long axis to the short axis is 3 to 2.

14. A sponge device comprising:
    a porous ovoid device having a long axis and a short axis;
    a passage of a predetermined diameter located along the long axis of the ovoid device and placed completely through said device;
    a chord extending through said passage and attached to the ovoid device by an attachment means;
    a medicament solution placed within the pores throughout the ovoid device; and
    a lubricant applied to the surface of said device.

15. The sponge device as recited in claim 14, wherein said attachment means is an anchor configuration.

16. The sponge device as recited in claim 14, wherein said attachment means is a button configuration.

17. The sponge device as recited in claim 14, wherein said attachment means is an umbrella configuration.

18. The sponge device as recited in claim 14, wherein said attachment means is a bottlecap configuration.

19. The sponge device as recited in claim 14, wherein the ratio of the long axis to the short axis is 3 to 2.

20. A sponge device configured for insertion by a user into a body cavity comprising:
    a porous ovoid device impregnated with medicament solution, optionally coated with a lubricant, and a first passage placed within or through said device; and
    a chord placed through said first passage and anchored within a portion of said ovoid device, said device capable of facilitating extraction, when utilized.

* * * * *

UNITED STATES PATENT AND TRADEMARK OFFICE
CERTIFICATE OF CORRECTION

PATENT NO. : 6,155,259
DATED : December 5, 2000
INVENTOR(S) : Conte et al.

Page 1 of 1

It is certified that error appears in the above-identified patent and that said Letters Patent is hereby corrected as shown below:

<u>Column 6,</u>
Delete lines 22 through 31.
Lines 32, 42, 44, 46, 48, and 50, delete "14" and replace with -- 9 --.

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*